(12) United States Patent
Liu et al.

(10) Patent No.: US 9,722,252 B2
(45) Date of Patent: Aug. 1, 2017

(54) ELECTRONICALLY CONDUCTIVE POLYMER BINDER FOR LITHIUM-ION BATTERY ELECTRODE

(71) Applicants: Gao Liu, Piedmont, CA (US); Shidi Xun, Pinole, CA (US); Vincent S. Battaglia, San Anselmo, CA (US); Honghe Zheng, Suzhou (CN); Mingyan Wu, Albany, CA (US)

(72) Inventors: Gao Liu, Piedmont, CA (US); Shidi Xun, Pinole, CA (US); Vincent S. Battaglia, San Anselmo, CA (US); Honghe Zheng, Suzhou (CN); Mingyan Wu, Albany, CA (US)

(73) Assignee: The Regents of the University of California, Oakland, CA (US)

( * ) Notice: Subject to any disclaimer, the term of this patent is extended or adjusted under 35 U.S.C. 154(b) by 91 days.

(21) Appl. No.: 14/790,299

(22) Filed: Jul. 2, 2015

(65) Prior Publication Data
US 2015/0311529 A1 Oct. 29, 2015

Related U.S. Application Data

(63) Continuation of application No. 13/615,402, filed on Sep. 13, 2012, now Pat. No. 9,077,039, which is a (Continued)

(51) Int. Cl.
*H01B 1/00* (2006.01)
*C07D 221/00* (2006.01)
(Continued)

(52) U.S. Cl.
CPC ............ *H01M 4/622* (2013.01); *B82Y 30/00* (2013.01); *C07D 221/00* (2013.01); *C08G 61/02* (2013.01); *C08J 5/005* (2013.01); *C08K 3/08* (2013.01); *C08L 65/00* (2013.01); *H01B 1/128* (2013.01); *H01M 4/134* (2013.01); *H01M 4/386* (2013.01);
(Continued)

(58) Field of Classification Search
CPC . H01B 1/00; H01B 1/12–1/128; C08G 61/00; C08G 61/02; C07D 221/00
See application file for complete search history.

(56) References Cited

U.S. PATENT DOCUMENTS

| 8,852,461 B2 * | 10/2014 | Liu | B82Y 30/00 252/500 |
|---|---|---|---|
| 9,077,039 B2 * | 7/2015 | Liu | C07D 221/00 |
| 9,153,353 B2 * | 10/2015 | Liu | H01M 4/622 |

* cited by examiner

*Primary Examiner* — Mark Kopec
(74) *Attorney, Agent, or Firm* — Lawrence Berkeley National Laboratory

(57) ABSTRACT

A family of carboxylic acid groups containing fluorene/fluorenon copolymers is disclosed as binders of silicon particles in the fabrication of negative electrodes for use with lithium ion batteries. Triethyleneoxide side chains provide improved adhesion to materials such as, graphite, silicon, silicon alloy, tin, tin alloy. These binders enable the use of silicon as an electrode material as they significantly improve the cycle-ability of silicon by preventing electrode degradation over time. In particular, these polymers, which become conductive on first charge, bind to the silicon particles of the electrode, are flexible so as to better accommodate the expansion and contraction of the electrode during charge/discharge, and being conductive promote the flow battery current.

2 Claims, 12 Drawing Sheets

GENERIC FORMULA FOR COPOLYMER BINDER $0 <= x, x', y$ and $z <= 1$ and $x + x' + y + z = 1$,
$R_1$ and $R_2$ can be $(CH_2)nCH_3$ with $n = 0 - 8$,
$R_3$ and $R_4$ can be $(CH_2)nCOOH$ with $n = 0 - 8$,
$R_5$ and $R_6$ can be any combination of H,
COOH and COOCH$_3$

Related U.S. Application Data continuation-in-part of application No. 13/294,885, filed on Nov. 11, 2011, now Pat. No. 8,852,461, which is a continuation of application No. PCT/US2010/035120, filed on May 17, 2010.

(60) Provisional application No. 61/179,258, filed on May 18, 2009, provisional application No. 61/243,076, filed on Sep. 16, 2009.

(51) Int. Cl.

| | | |
|---|---|---|
| *H01M 4/62* | (2006.01) | |
| *H01B 1/12* | (2006.01) | |
| *B82Y 30/00* | (2011.01) | |
| *C08J 5/00* | (2006.01) | |
| *C08G 61/02* | (2006.01) | |
| *C08K 3/08* | (2006.01) | |
| *H01M 4/134* | (2010.01) | |
| *H01M 4/38* | (2006.01) | |
| *C08L 65/00* | (2006.01) | |
| *H01M 10/0525* | (2010.01) | |

(52) U.S. Cl.
CPC ............ *C08G 2261/1414* (2013.01); *C08G 2261/1424* (2013.01); *C08G 2261/1426* (2013.01); *C08G 2261/312* (2013.01); *C08G 2261/3142* (2013.01); *C08G 2261/516* (2013.01); *C08J 2365/00* (2013.01); *H01M 10/0525* (2013.01); *Y02E 60/122* (2013.01)

GENERIC FORMULA FOR COPOLYMER BINDER $0 \leq x, x', y$ and $z \leq 1$ and $x + x' + y + z = 1$,
$R_1$ and $R_2$ can be $(CH_2)nCH_3$ with $n = 0 - 8$,
$R_3$ and $R_4$ can be $(CH_2)nCOOH$ with $n = 0 - 8$,
$R_5$ and $R_6$ can be any combination of H,
COOH and $COOCH_3$ Capacity change based on cycling number.

Coulombic efficiency according to cycling number.

Voltage profile of the Si electrode during lithium insertion and removal

Si electrode cycling behavior at fixed capacity.

Cycling results for PFFOMB in a different electrolyte

ELECTRONICALLY CONDUCTIVE POLYMER BINDER FOR LITHIUM-ION BATTERY ELECTRODE

CROSS REFERENCE TO RELATED APPLICATIONS

This application is a continuation of U.S. application Ser. No. 13/615,402, filed Sep. 13, 2012, now U.S. Pat. No. 9,077,039, which is a continuation-in-part of U.S. application Ser. No. 13/294,885, filed Nov. 11, 2011, now U.S. Pat. No. 8,852,461, which is a national phase entry under 35 U.S.C. §371 of PCT Application No. PCT/US2010/035120, filed May 17, 2010, which claims priority to U.S. Provisional Application Ser. No. 61/179,258 filed May 18, 2009, and U.S. Provisional Application Ser. No. 61/243,076 filed Sep. 16, 2009.

STATEMENT OF GOVERNMENTAL SUPPORT

The invention described and claimed herein was made in part utilizing funds supplied by the U.S. Department of Energy under Contract No. DE-AC02-05CH11231. The government has certain rights in this invention.

BACKGROUND OF THE INVENTION

Field of the Invention

This invention relates generally to lithium ion batteries, and more specifically to an improved polymeric binder for forming silicon electrodes resulting in battery electrodes of increased charge density.

Background of the Invention

Lithium-ion batteries are a type of rechargeable battery in which lithium ions move between the negative and positive electrode. The lithium ion moves through an electrolyte from the negative to the positive during discharge, and in reverse, from the positive to the negative, during recharge. Most commonly the negative electrode is made of graphite, which material is particularly preferred due to its stability during charge and discharge cycles as it forms solid electrolyte interface (SEI) layers with very small volume change.

Lithium ion batteries and finding ever increasing acceptance as power sources for portable electronics such as mobile phones and laptop computers that require high energy density and long lifetime. Such batteries are also finding application as power sources for automobiles, where recharge cycle capability and energy density are key requirements. In this regard, research is being conducted in the area of improved electrolytes, and improved electrodes. High-capacity electrodes for lithium-ion batteries have yet to be developed in order to meet the 40-mile plug-in hybrid electric vehicle energy density needs that are currently targeted.

One approach is to replace graphite as the negative electrode with silicon. Notably graphite electrodes are rated at 372 mAh/g (milliamp hours per gram) at $LiC_6$, while silicon electrodes are rated more than tenfold better at 4,200 mAh/g at $Li_{4.4}Si$. However, numerous issues prevent this material from being used as a negative electrode material in lithium-ion batteries. Full capacity cycling of Si results in significant capacity fade due to a large volume change during Li insertion (lithiation) and removal (de-lithiation). This volumetric change during reasonable cycling rates induces significant amounts of stress in micron size particles, causing the particles to fracture. Thus an electrode made with micron-size Si particles has to be cycled in a limited voltage range to minimize volume change.

Decreasing the particle size to nanometer scale can be an effective means of accommodating the volume change. However, the repeated volume change during cycling can also lead to repositioning of the particles in the electrode matrix and result in particle dislocation from the conductive matrix. This dislocation of particles causes the rapid fade of the electrode capacity during cycling, even though the Si particles are not fractured. Novel nano-fabrication strategies have been used to address some of the issues seen in the Si electrode, with some degree of success. However, these processes incur significantly higher manufacturing costs, as some of the approaches are not compatible with current Li ion manufacture technology. Thus, there remains the need for a simple, efficient and cost effective means for improving the stability and cycle-ability of silicon electrodes for use in Lithium ion batteries.

SUMMARY OF INVENTION

By way of this invention, a new class of binder materials has been designed and synthesized to be used in the fabrication of silicon containing electrodes. These new binders, which become conductive on first charge, provide improved binding force to the Si surface to help maintain good electronic connectivity throughout the electrode, to thus promote the flow of current through the electrode. The electrodes made with these binders have significantly improved the cycling capability of Si, due in part to their elasticity and ability to bind with the silicon particles used in the fabrication of the electrode.

More particularly, we have found that a novel class of conductive polymers can be used as conductive binders for the anode electrode. These polymers include poly 9,9-dioctylfluorene and 9-fluorenone copolymer. The polyfluorene polymer can be reduced around 1.0 V (vs. lithium metal potential) and becomes very conductive from 0-1.0 V. Since negative electrodes (such as Si) operate within a 0-1.0 V window, this allows polyfluorene to be used as an anode binder in the lithium ion battery to provide both mechanical binding and electric pathways. As a unique feature of this polymer, by modifying the side chain of the polyfluorene conductive polymer with functional groups such as —COOH that will bond with Si nanocrystals, significantly improved adhesion can be realized.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION

Figure 1:
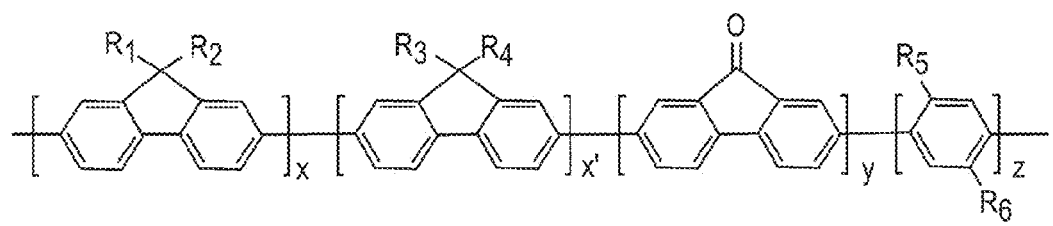
FIG. 1 depicts a generic chemical formula of a conductive polymer binder according to an embodiment of the present invention.

According to this invention the conductive polymers developed herein act as a binder for the silicon particles used for the construction of the negative anode. They are mixed with the silicon nano sized silicon parties in a slurry process, then coated on a substrate such as copper or aluminum and thereafter allowed to dry to form the film electrode. Though the silicon particles can range from micron to nano size, the use of nano sized particles is preferred as such results in an electrode material that can better accommodate volume changes.

A fabrication method for the synthesis of one embodiment of the binder polymer of this invention is as set forth below. First presented is a means for preparing one of the monomers used in polymer formation, i.e. 2,5-dibromo-1,4-benzenedicarboxylic acid, a reaction scheme for preparing this monomer illustrated immediately below.

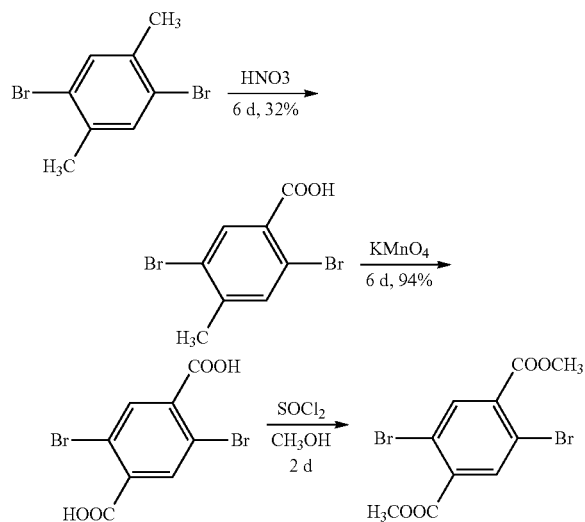

When the benzenedicarboxylic acid staring material has only one $CH_3$ group, the reaction will end up with only one $R=COOCH_3$ group in the final product.

A. Synthesis of polymeric PFFO (poly(9,9-dioctylfluorene-co-fluorenone))

Exemplary of a method for forming one of the polymers of this invention is provided with respect to one embodiment, according to the reaction scheme set forth below. A mixture of 9,9-dioctylfluorene-2,7-diboronic acid bis(1,3-propanediol) ester (0.83 g, 1.5 mmol) commercially available from Sigma-Aldrich Company, 2,7-dibromo-9-fluorenone (0.50 g, 1.5 mmol), $(PPh_3)_4Pd(0)$ (0.085 g, 0.07 mmol) and several drops of aliquat 336 in a mixture of 10 mL of THF (tetrahydrofuran) and 4.5 mL of 2 M $Na_2CO_3$ solution was refluxed with vigorous stirring for 72 hours under an argon atmosphere. During the polymerization, a brownish solid precipitated out of solution. The solid was collected and purified by Soxhlet extraction with acetone as solvent for two days with a yield of 86%.

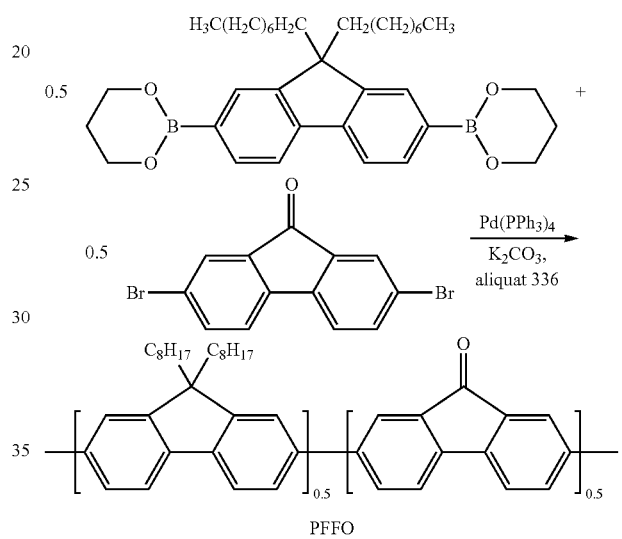

PFFO

B. Synthesis of PFFOMB (poly(9,9-dioctylfluorene-co-fluorenone-co-methylbenzoic acid))

A mixture of 9,9-dioctylfluorene-2,7-diboronic acid bis (1,3-propanediol) ester (0.80 g, 1.43 mmol), 2,7-dibromo-9-fluorenone (0.24 g, 0.72 mmol), methyl 2,5-dibromobenzoate (0.21 g, 0.72 mmol), $(PPh_3)_4Pd(0)$ (0.082 g, 0.072 mmol) and several drops of Aliquat 336 in a mixture of 13 mL of THF (tetrahydrofuran) and 5 mL of 2 M $Na_2CO_3$ solution was refluxed with vigorous stirring for 72 h under an argon atmosphere. After reaction stopped, the solution was concentrated by vacuum evaporation and the polymer was precipitated from methanol. The resulting polymer was further purified by precipitating from methanol twice. The final polymer was collected by suction filtration and dried under vacuum with a yield of 87%.

C. Synthesis of PFFOBA (poly(9,9-dioctylfluorene-co-fluorenone-co-benzoic acid))

A mixture of PFFOMB (0.36 g) and KOH (2 g, 35 mmol) in 20 mL of THF and 2 mL of $H_2O$ was refluxed for 48 h under an argon atmosphere. After reaction stopped, the solution was concentrated by vacuum evaporation and polymer was precipitated from methanol. The resulting polymer was suspended in 10 mL of concentrated $H_2SO_4$ with vigorous stirring for 12 hours. The final product was filtered, washed with water and dried with a yield of 96%.

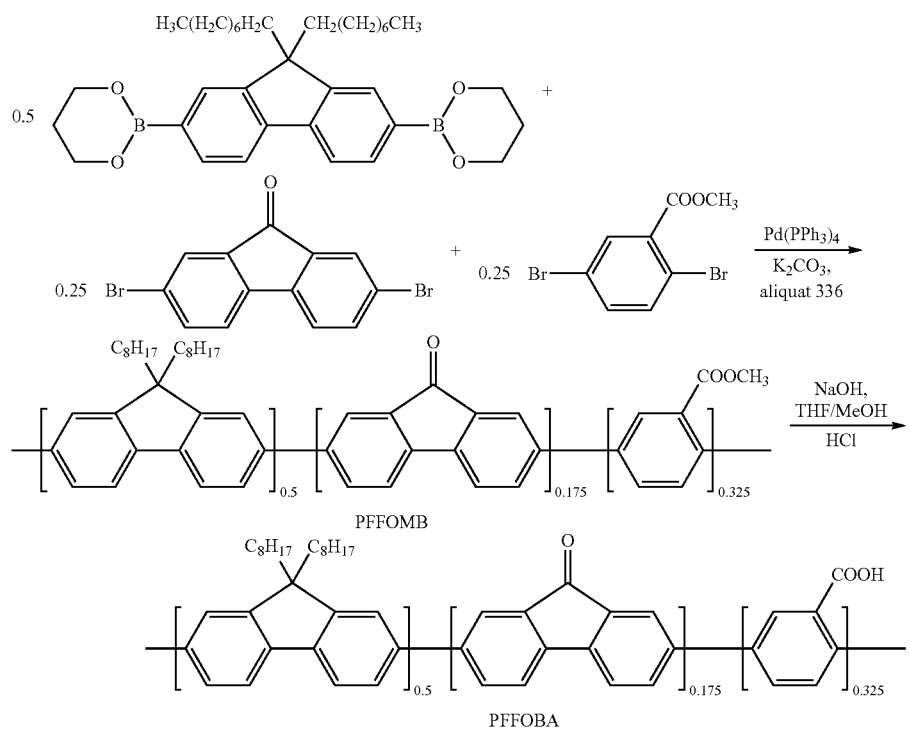

Reaction scheme for forming conductive polymer with —COOCH₃ (PFFOMB) and —COOH (PFFOBA) groups on the side chains.

It has been found that the presence of —COOH groups serves to increase the bindability of the polymer to the silicon particles of the electrode. In particular, one can position carboxylic acid groups in connection with the 9$^{th}$ position of fluorene backbone. The below formula depicts the general structure of this type of polymer.

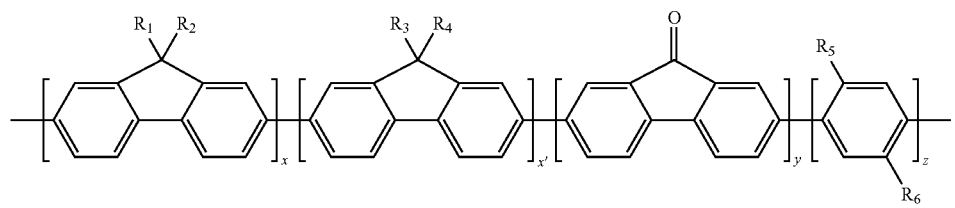

Wherein x=0, x' and y=>0, and z<=1, and x'+y+z=1, $R_3$ and $R_4$ can be $(CH_2)_n COOH$, n=0-8, and $R_5$ and $R_6$ can be any combination of H, COOH and COOCH₃.

Another variation is to adjust the number of COOH groups by copolymerizing x monomer into the main chains as illustrated in the formula shown below. By adjusting the ratio of x:x', the number of —COOH groups can be controlled without changing the electronic properties of the conductive binders. Exemplary of such a composition is as illustrated below by the following formula.

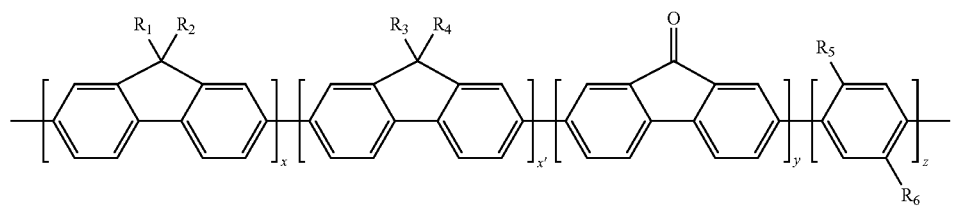

PFF'FOB

Herein, x, x', y>0, and z<=1, with x+x'+y+z=1. $R_1$ and $R_2$ can be $(CH_2)$—$CH_3$, n=0-8. $R_3$ and $R_4$ can be $(CH_2)_n$COOH, n=0-8. $R_5$ and $R_6$ can be any combination of H, COOH and $COOCH_3$; and the "x, x'" unit is fluorene with either alkyl or alkylcarboxylic acid at the 9, 9' positions; the "y" unit is fluorenone, The H positions of the back bone of fluorenon and fluorene also can be substituted with functional groups such as COOH, F, Cl, Br, $SO_3H$, etc.

In still another embodiment, one can increase the flexibility of the polymer by introducing a flexible section between repeating units. This is illustrated as shown below where a flexible chain section such as alkyl or polyethylene can be used to connect A sections together to further improve elasticity, the structure illustrated by the below formula:

where n>=0, and the A sections are defined as follows:

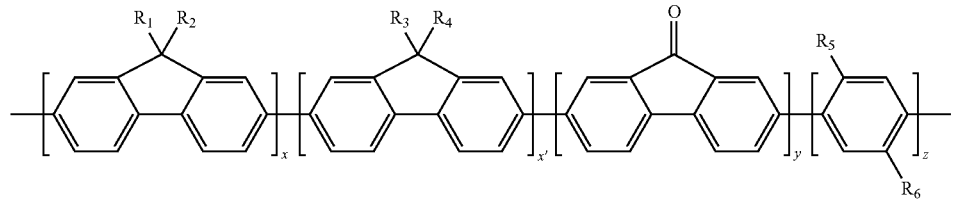

PFF'FOB

Wherein
0<=x, x', y and z<=1 and x+x'+y+z=1.
$R_1$ and $R_2$ can be $(CH_2)$—$CH_3$, n=0-8, $R_3$ and $R_4$ can be $(CH_2)$—COOH, n=0-8, $R_5$ and $R_6$ can be any combination of H, COOH and $COOCH_3$.

Most of the highly conjugated conductive polymers have rigid backbones, and the elasticity of the polymers is low. In order to accommodate volume expansion incurred during the Li interacalation and de-intercalation in the alloys, it is important that the conductive polymer binders have certain degree of elasticity. One method to increase flexibility is to synthetically introduce flexible units (n) into the polymer system as show above. Unit n is a flexible alkyl or polyethylene portion. This flexible unit (n) can be one or many of —$CH_2$ units depending upon the requirements for a particular alloy system, or could be other types of liner units depending on the ease of synthesis. Both x, x', y and z units could be one or many fluorene or fluorenone units. One possible structure is of a random copolymer with a few percent of flexible units distributed along the fluorene main chain. The $R_1$-$R_6$ units could be either one of the choices, and it is not necessary they be all the same in a polymer chain. Increasing the length of the side chains may also have an effect on the flexibility of the polymer binder. Therefore, the number of units in $R_1$-$R_6$ is also subject to change during an optimization process. One may change the number of units of the $R_1$-$R_6$, and look for improved cell cycling performance as indication of optimization.

Another issue is the stability and impedance of the interface between the active cathode material and electrolyte. The binder may cover (that is, over-coat) all the active materials at higher binder loadings. Such over-coverage will modify the interface stability and impedance. Varying the number of units in $R_1$-$R_6$ will play a significant role in optimizing the charge transfer impedance at the interface.

Current polymer structures that have been synthesized and tested in lithium ion battery are shown as illustrated by the below.

PFFO (poly(9,9-dioctylfluorene-co-fluorenone))

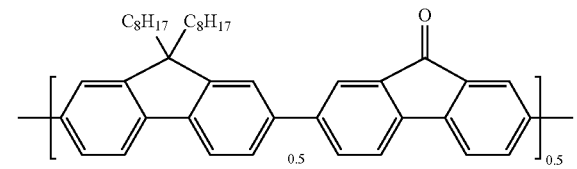

PFFOMB (poly(9,9-dioctylfluorene-co-fluorenone-co-methylbenzoic acid))

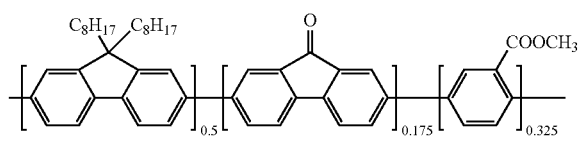

PFFOBA (poly(9,9-dioctylfluorene-co-fluorenone-co-benzoic acid))

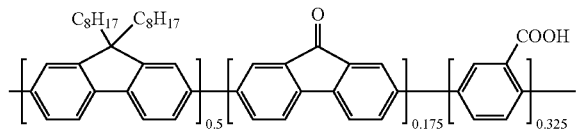

Once the conductive polymers have been synthesized they can be mixed with the silicon particles, and coated onto a substrate such as copper and allowed to dry to form the electrode material. A more detailed discussion of electrode preparation is presented below. An advantage of the use of these conductive polymers of the present invention is that they are easily compatible with current slurry processes for making electrodes, thus requiring no special steps or equipment.

Process for Making Slurry of Conductive Polymer

Si/conductive polymer mixtures were made by dissolving 0.09 g of the conductive polymer of FIG. 1 (i.e., PFFOBA, wherein $R_1$=$R_2$=$(CH_2)_7CH_3$, $R_5$=$COOCH_3$, $R_6$=H, and x=0.5, x'=0, y=0.175 and z=0.325)) in 2.6 g of chlorobenzene. 0.18 g of Si was dispersed in the polymer solution to meet the desired Si:polymer ratios at 2:1. To ensure the thorough mixing of the Si nanoparticles into the polymer solution, a Branson 450 sonicator equipped with a solid horn was used. The sonication power was set at 70%. A continuous sequence of 10 second pulses followed by 30 second rests was used. The sonic dispersion process took about 30 min. All of the mixing processes were performed in Ar-filled glove boxes.

Process for Making Conductive Glue of AB/PVDF

Figure 2:
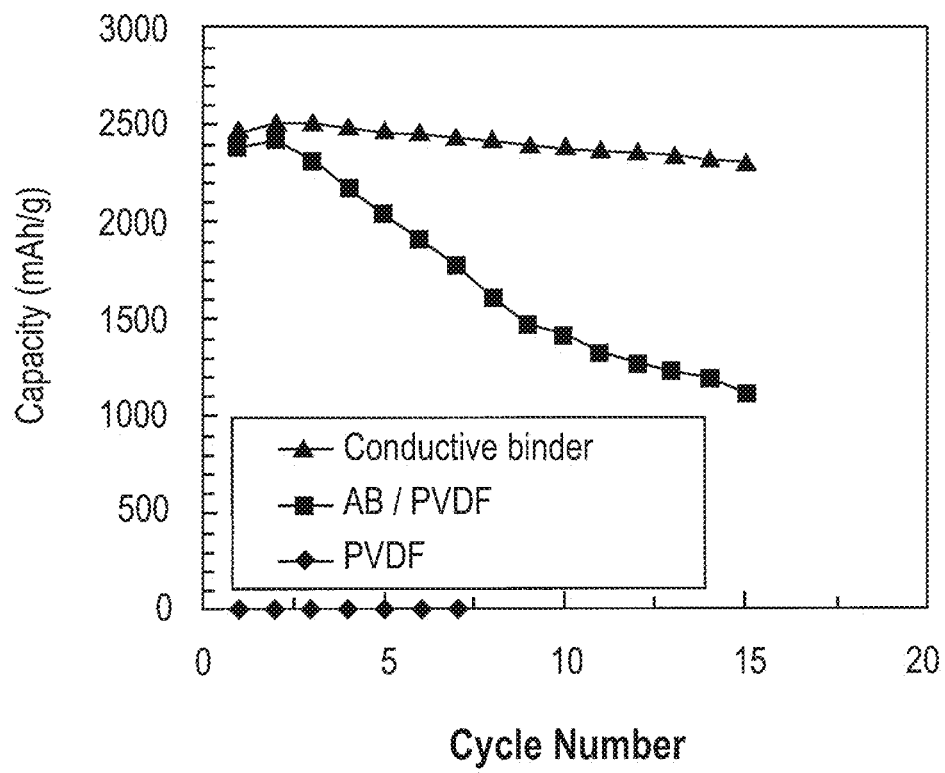
FIG. 2 is a plot of electrode capacity vs. cycle number for a Si anode made with the conductive binder of FIG. 1 according to one embodiment of the invention, wherein $R_1=R_2=(CH_2)_7CH_3$, $R_5=COOCH3$, $R_6=H$ and x=0.5, x'=0, y=0.175 and z=0.325.
Figure 3:
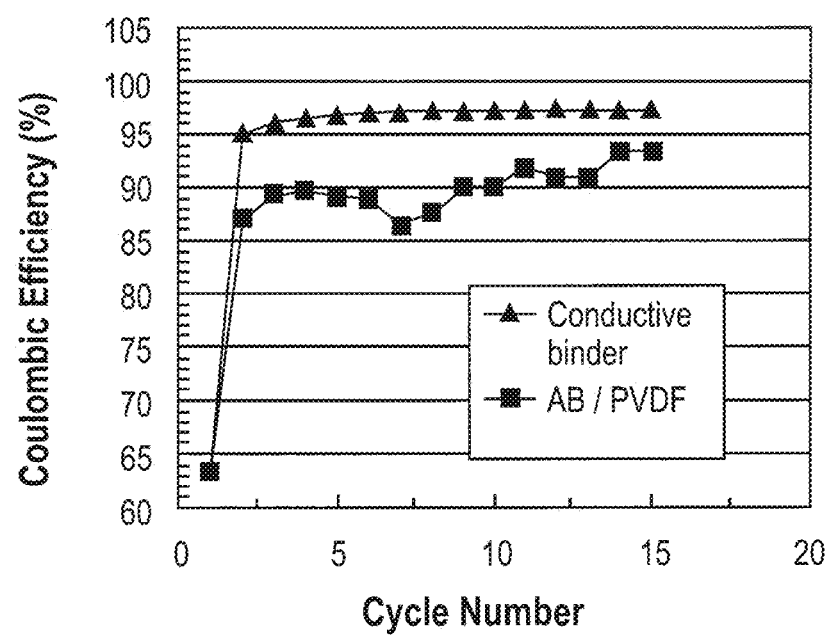
FIG. 3 is a plot of Coulombic Efficiency (%) vs. Cycle Number for the same Si anode/conductive binder electrode of FIG. 2.

By way of comparison to the conductive polymers of this invention, illustrated in FIGS. 2 and 3, slurries of AB:PVDF (acetylene black/polyvinylidene fluoride) at 0.2:1 ratios by weight were made by dissolving 5 g of PVDF in to 95 g of NMP to make a 5% PVDF in NMP solution. Proper amounts of AB was dispersed in the PVDF solution to meet the desired AB:PVDF ratios. To ensure the thorough mixing of the AB nanoparticles into the PVDF solution, the Branson 450 sonicator equipped with a solid horn was used. The sonication power was set at 70%. A continuous sequence of 10 s pulses followed by 30 s rests was used. The sonic dispersion process took ca. 30 min. All of the mixing processes were performed in Ar-filled glove boxes.

Process for Making Slurry of Si/AB/PVDF 0.86 g Si was mixed with 7.16 g of the conductive glue (PVDF:AB=1:0.2 by weight in 95% PVDF NMP solution). To ensure the thorough mixing of the Si nanoparticles into the glue solution, the Branson 450 sonicator equipped with a solid horn was used. The sonication power was set at 70%. A continuous sequence of 10 s pulses followed by 30 s rests was used. The sonic dispersion process took about 30 min. All of the mixing processes were performed in Ar-filled glove boxes.

Process for Making the Electrode

All electrode laminates were cast onto a 20 μm thick battery-grade Cu sheet using a Mitutoyo doctor blade and a Yoshimitsu Seiki vacuum drawdown coater to roughly the same loading per unit area of active material. The films and laminates were first dried under infrared lamps for 1 h until most of the solvent was evaporated and they appeared dried. The films and laminates were further dried at 120° C. under $10^{-2}$ Torr dynamic vacuum for 24 h. The film and laminate thicknesses were measured with a Mitutoyo micrometer with an accuracy of ±1 μm. The typical thickness of film is about 20 μm. The electrodes were compressed to 35% porosity before coin cell assembly using a calender machine from International Rolling Mill equipped with a continuously adjustable gap.

Process for Fabricating Coin Cell

Coin cell assembly was performed using standard 2325 coin cell hardware. A 1.47 cm diameter disk was punched out from the laminate for use in the coin cell assembly as a working electrode. Lithium foil was used in making the counter electrode. The counter electrodes were cut to 1.5 cm diameter disks. The working electrode was placed in the center of the outer shell of the coin cell assembly and two drops of 1 M $LiPF_6$ in EC:DEC (1:1 weight ratio) electrolyte purchased from Ferro Inc. were added to wet the electrode. A 2 cm diameter of Celgard 2400 porous polyethylene separator was placed on top of the working electrode. Three more drops of the electrolyte were added to the separator. The counter electrode was placed on the top of the separator. Special care was taken to align the counter electrode symmetrically above the working electrode. A stainless steel spacer and a Belleville spring were placed on top of the counter electrode. A plastic grommet was placed on top of the outer edge of the electrode assembly and crimp closed with a custom-built crimping machine manufactured by National Research Council of Canada. The entire cell fabrication procedure was done in an Ar-atmosphere glove box.

Process for Testing Coin Cell

The coin cell performance was evaluated in a thermal chamber at 30° C. with a Maccor Series 4000 Battery Test System. The cycling voltage limits were set at 1.0 V at the top of the charge and 0.01 V at the end of the discharge.

Chemicals

All the starting chemical materials for synthesis of the conductive polymer were purchased from Sigma-Aldrich. Battery-grade AB with an average particle size of 40 nm, a specific surface area of 60.4 $m^2/g$, and a material density of 1.95 $g/cm^3$ was acquired from Denka Singapore Private Ltd. PVDF KF1100 binder with a material density of 1.78 $g/cm^3$ was supplied by Kureha, Japan. Anhydrous N-methylpyrrolidone NMP with 50 ppm of water content was purchased from Aldrich Chemical Co.

As described above, the conductive polymers of this invention can be used as electrically conductive binders for Si nanoparticles electrodes. The electron withdrawing units lowering the LUMO level of the conductive polymer make it prone to reduction around 1 V against a lithium reference, and the carboxylic acid groups provide covalent bonding with OH groups on the Si surface by forming ester bonds. The alkyls in the main chain provide flexibility for the binder.

Figure 4:
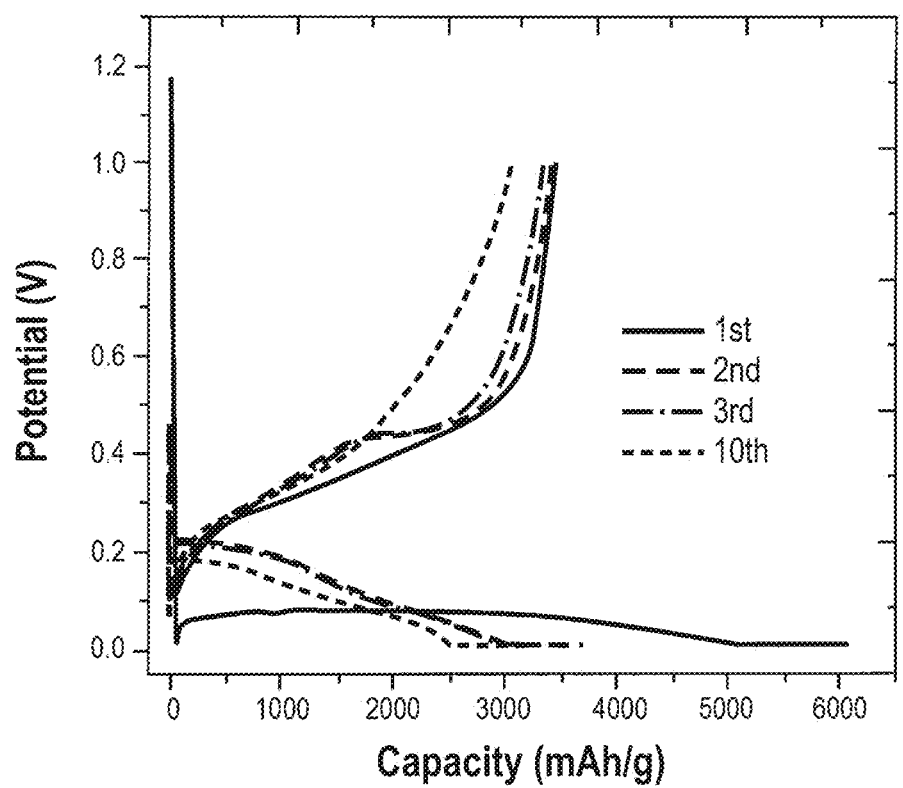
FIG. 4 shows the voltage profile of the electrode of FIG. 2 in the first several cycles of lithium insertion and removal.
Figure 5:
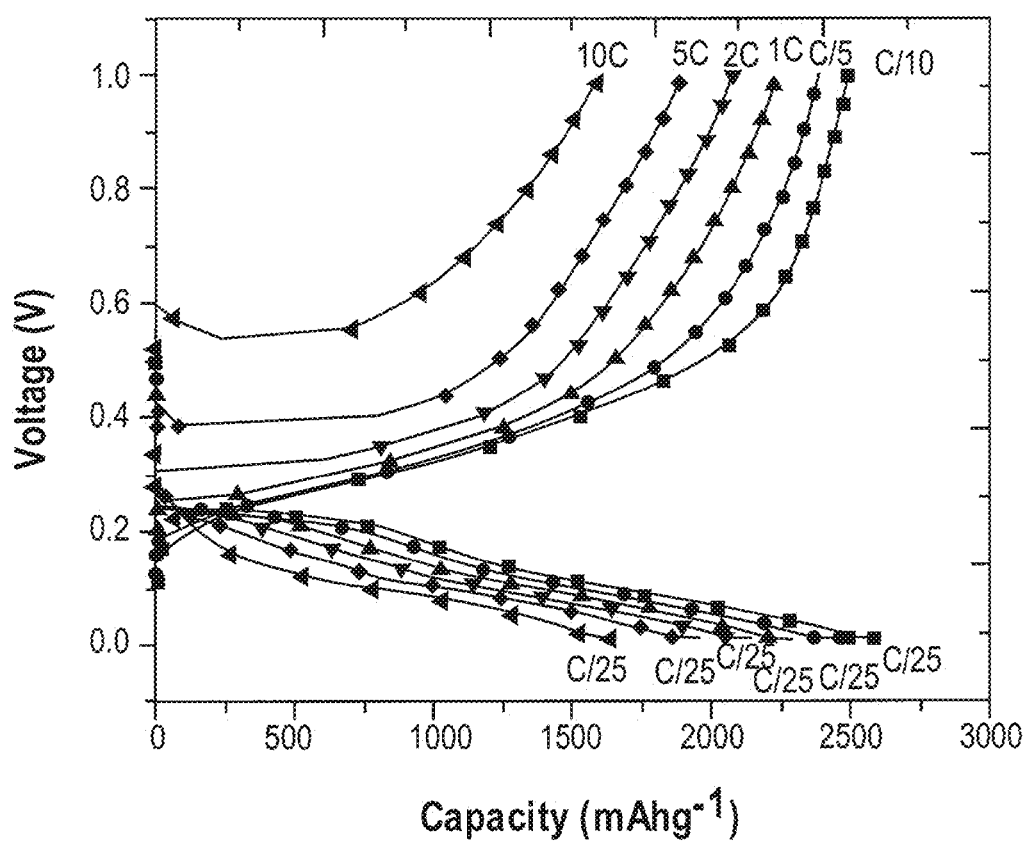
FIG. 5 shows the de-lithiation performance of the same electrode at different charge-rates.
Figure 6:
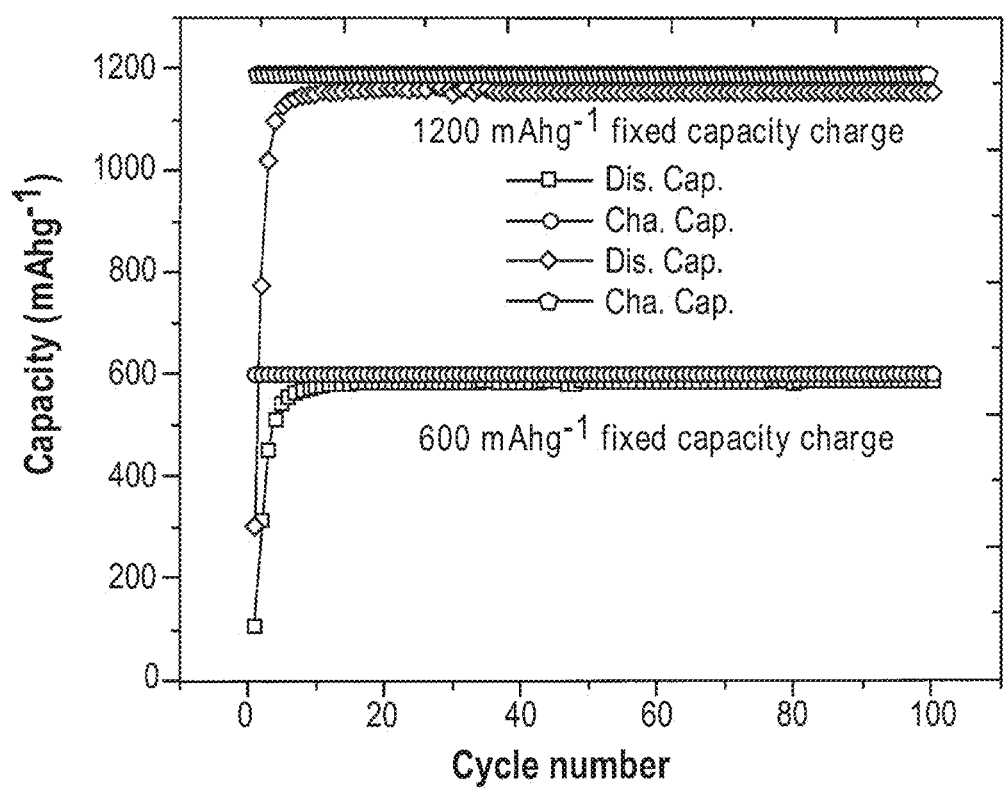
FIG. 6 is a plot of Si electrode cycling behavior at fixed capacity for the electrode of FIG. 2. When the lithiation is limited to a selected capacity, the de-lithiation capacities are stable in 100 cycles as shown.
Figure 7:
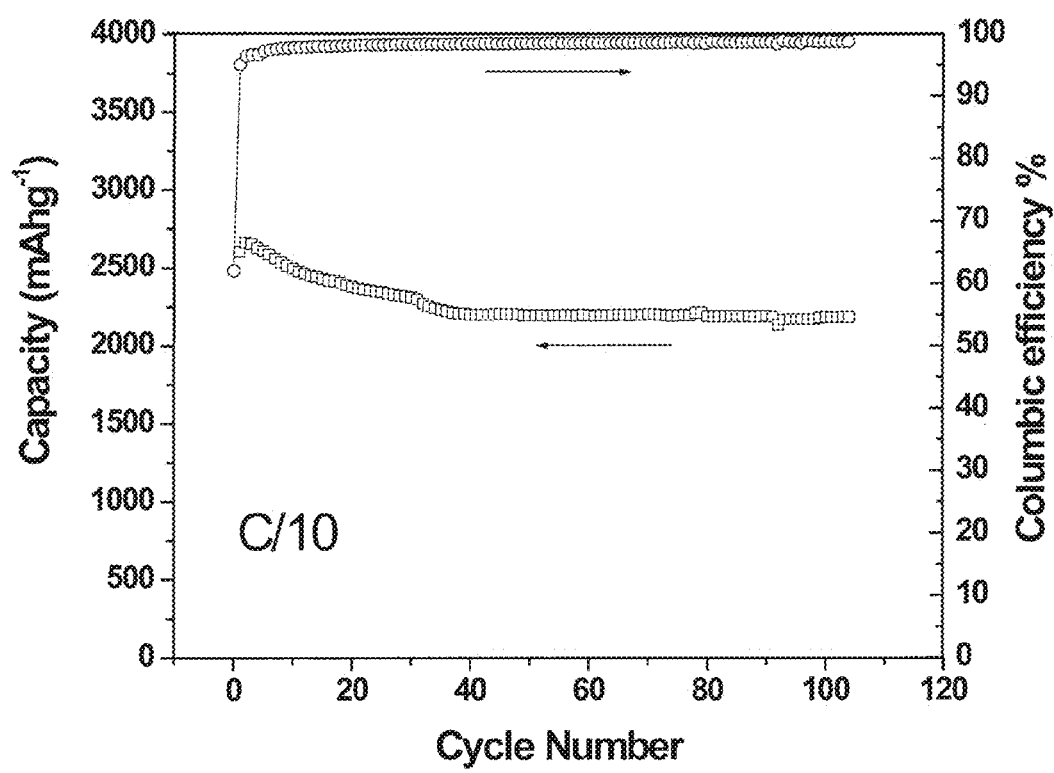
FIG. 7 is a plot of cycling results for a PFFOMB (poly(9,9-dioctylfluorene-co-fluorenone-co-methylbenzoic acid)) binder used in combination with an electrolyte comprising $LiPF_6$ in EC/DEC+10% FEC.

Results of the various tests that were conducted are as reported in the various plots of FIGS. 2-6. FIG. 2 shows the new conductive polymer binder in combination with Si nanoparticles much improving the capacity retention compared to conventional acetylene black (AB) and polyvinylidene difluride (PVDF) conductive additive and binder as a control. FIG. 3 illustrates the improved coulombic efficiency of the conductive binder/Si electrode of the invention compared with the conventional AB/PVDF approach. FIG. 4 illustrates results showing very similar voltage profiles of the conductive polymer/Si electrode to the pure Si film type of electrode. FIG. 5 plots the rate performance of the conductive polymer/Si electrode of the invention, showing good results. Evan at a 10 C rate, there is still more than half of the capacity retention. Finally, FIG. 6 illustrates cycleability of the silicon electrode made with the copolymer binder of the invention, which is very good at limited capacity range. There is no capacity fade in 100 cycles at 1200 mAh/g and 600 mAh/g fixed capacity cycling. FIG. 7 illustrates cycling results for a PFFOMB binder using an electrolyte comprising 1.2 M LiPF6 in EC/DEC (ethylene carbonate and diethylene carbonate) plus 10% FEC (fluroethylene carbonate or fluorinated ethylene carbonate), the FEC additive serving as a stabilizer.

C. Synthesis of PFPFOFOMB (poly(2,7-9,9-dioctylfluorene-co-2,7-9,9-(di(oxy-2,5,8-trioxadecane)) fluorine-co-2,7-fluorenone-co-2,5-1-methylbenzoic ester)) (an analog of PFFOMB) binder and the Si electrode performance Triethyleneoxide side chains provide improved adhesion to materials such as, graphite, silicon, silicon alloy, tin, tin alloy. Additionally triethyleneoxide side chains provide a higher swelling rate that improves ionic conduction. In one embodiment, a 30% weight increase above dry weight provides an increase in ionic conduction while also avoiding bursting of the battery.

Scheme 1. Monomer synthesis

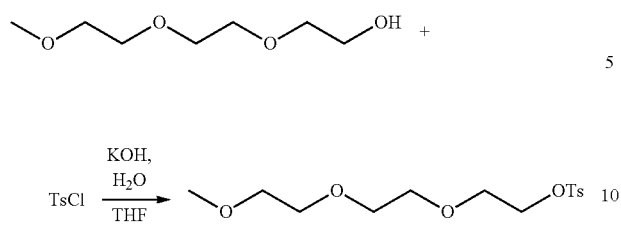

Scheme 2. Generic structure of monomer syntheis

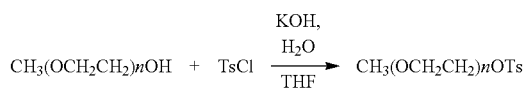

Scheme 1 lists the synthetic process to form the tosylated triethyleneoxide methylether.

The number of ethyleneoxide units can vary from 0 to 10000 (n=0-10000), and n can be an exact number or an average. The higher number of n is called an oligoethyleneoxide monomethylether. Scheme 2 gives the generic structure of a possible family of the tosylate products. The typical number of n is from 1-5.

Scheme 3. Synthesis of the PFO monomer with triethyleneoxide side chains

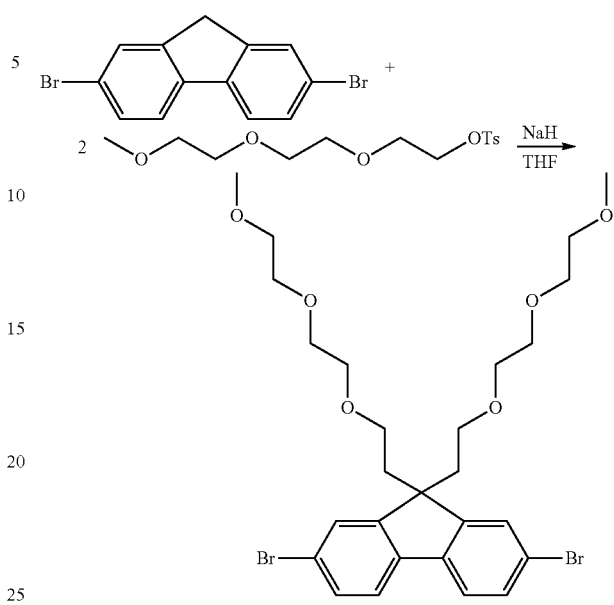

Scheme 3 is the schematic process of synthesis of the PFO monomer using tosylated triethlyeneoxide monomethylether. Tosylate with other oligothyleneoxide monomethylether as in Scheme 2 can also be used to form different lengths of ethyleneoxide chains at the 9 positions of the fluorene.

Scheme 4. Synthesis of PFPFOFOMB and PFPFOFOBA process

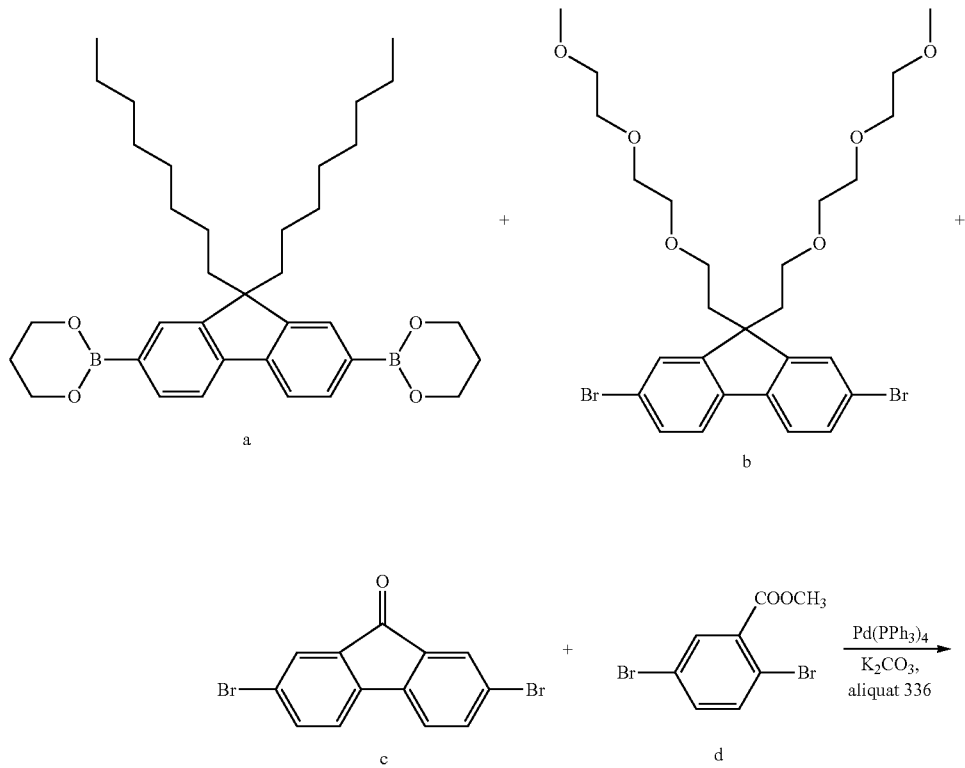

-continued

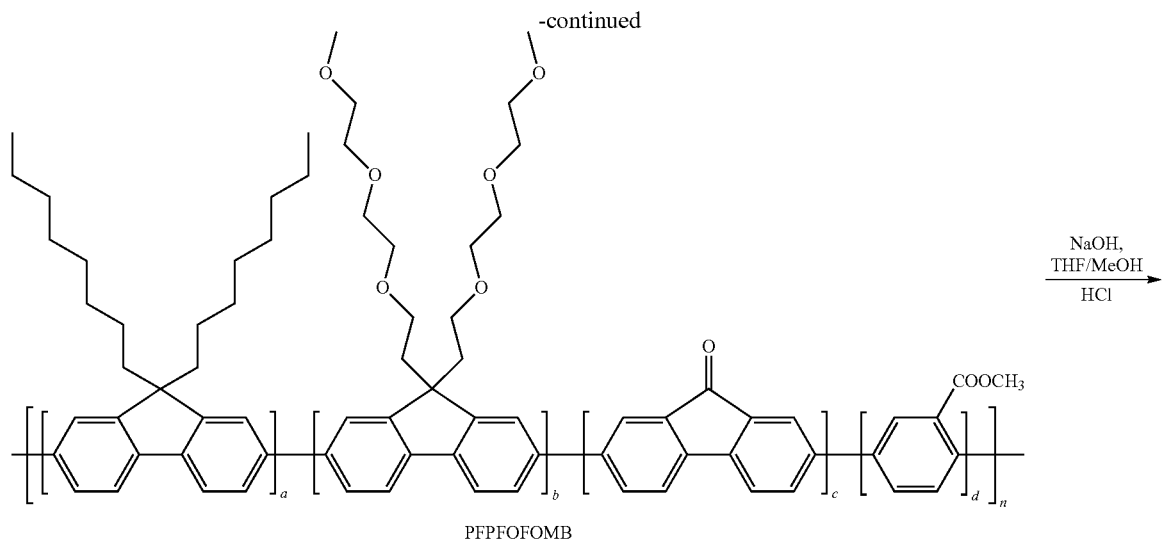

PFPFOFOMB

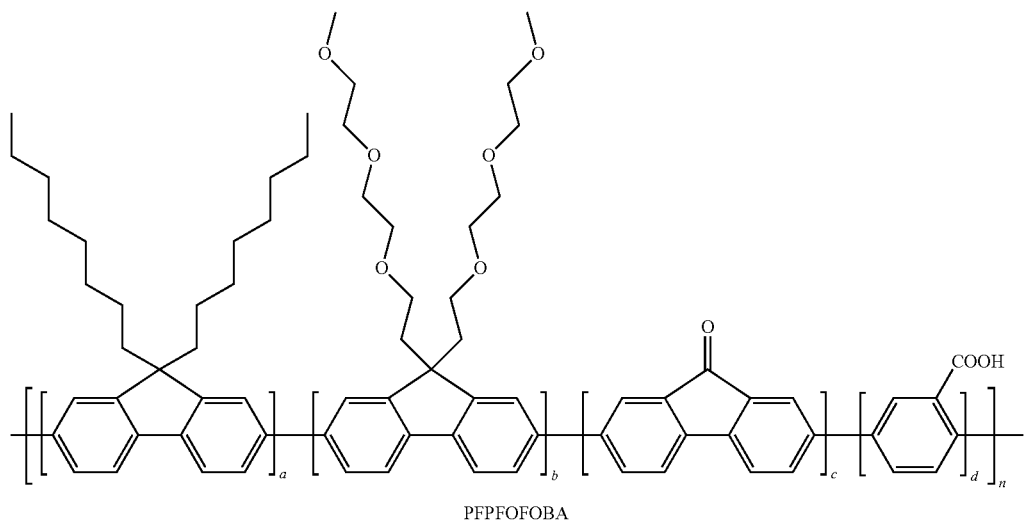

PFPFOFOBA

Figure 12:
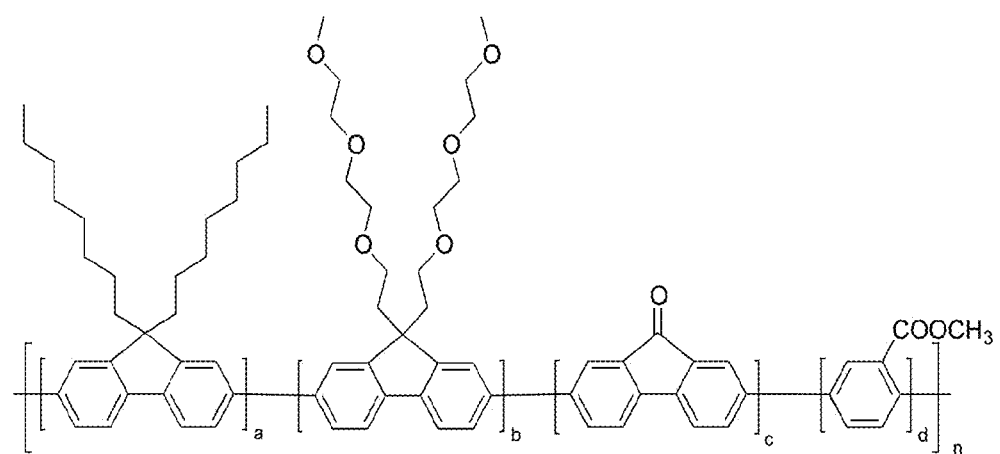
FIG. 12 illustrates the PFPFOFOMB.

The PFO monomer can be incorporated into the PFFOMB polymer binder (IB-2643) in the process described in Scheme 4. FIG. 12 illustrates the PFPFOFOMB. Both PFPFOFOMB and PFPFOFOBA are random copolymers, where all the units are located randomly. The subscribed numbers in the polymer molecular structure indicates the ratios among all the units. This synthesis process requires to have a=b+c+d. The composition we used to generate the polymer PFPFOFOMA is a=3, b=1, c=1 and d=1, so the ratio between the Octylfluorene (segment a) and triethyleneoxide fluorene (segment b) is 3/1. The segment b has higher polarity due to the triethyleneoxide chains therefore increases electrolyte uptake and improved adhesion between the particle surfaces and the binder. With synthetic Scheme 4, a, b, c, and d can vary from 0-1000 as long as the condition of a=b+c+d is satisfied.

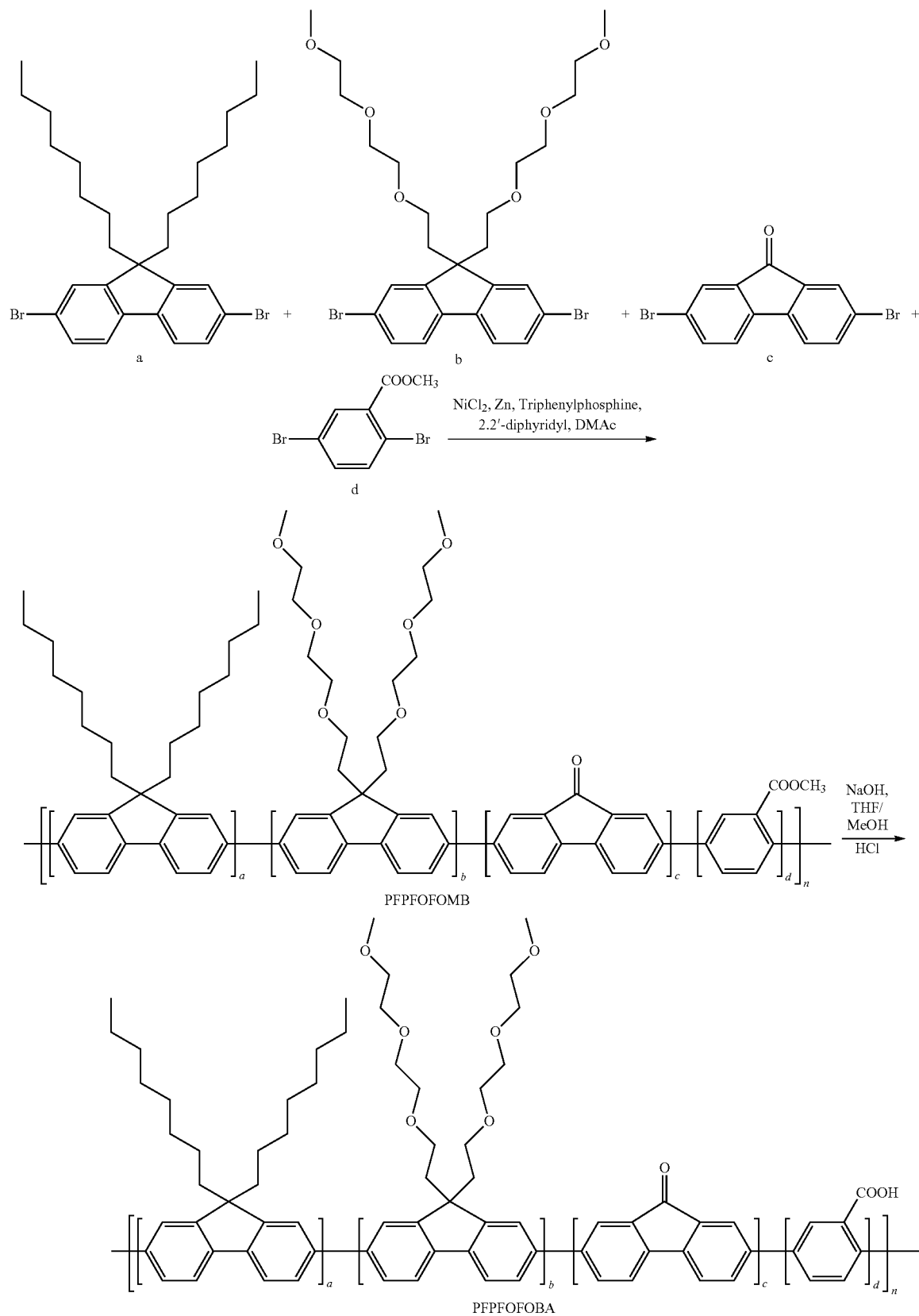
Scheme 5. An alternative synthesis process to make PFPFOFOMB and PFPFOFOBA Scheme 5 is an alternative synthesis process to make both PFPFOFOMB and PFPFOFOBA polymers. This alternative process does not have the constraint as the process described in Scheme 4. Therefore, a, b, c, d can be another number between 0-1000. The alternation of the numbers has a major impact of the binder when combined with silicon.

The above binder is combined with Si (Sn or other alloy of the kind) particles to formulate a lithium ion negative electrode. The particle can be spherical, a wire, or a plate. For spherical or pseudo spherical particles, the diameter can be from 0.1 nm-100 micron. For wires, the spherical cross-section is in 0.1 nm-100 micron. The length is 1 nm-1000 micron. For a plate, the thickness is in 0.1 nm-100 micron. The plain size is also 0.1 nm-100 micron. The binder and particle composites contain at least one particle.

2,7-Dibromo-9,9(di(oxy-2,5,8-trioxadecane))fluorene 2,7-dibromofluorene (5.0 g, 15.4 mmol) was dissolved in dried THF solution (30 mL). Sodium hydride (1.0 g, 40 mmol) was added to the THF solution at room temperature and refluxed for 5 hours. 10-Tosyloxy-2,5,8-trioxadecane (11.8 g, 37 mmol) in 20 mL of dry THF was added dropwise to the refluxed solution. The mixture was allowed to refluxed over night, then cooled down, poured into distill water and extracted with chloroform (2×100 mL). The combined organic solutions were washed with saturated NaCl solution (2×100 mL), distilled water (1×100 mL), dried over $MgSO_4$, and concentrated under reduced pressure. Crude oil was further purified by column chromatography using hexane/

Scheme 6. The synthesized polymer

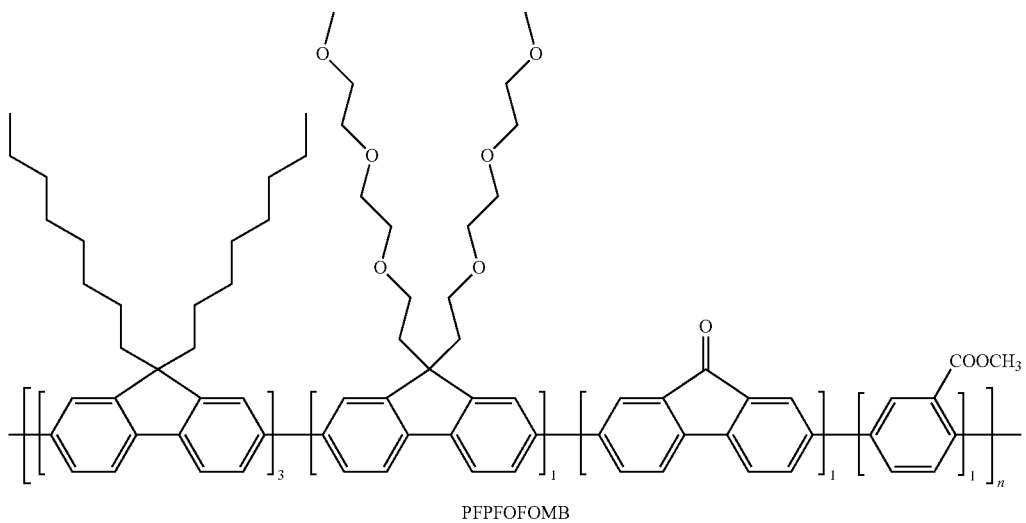

PFPFOFOMB

The polymer synthesized is demonstrated in Schematic 6. This polymer is combined with Si nanoparticles. The Si nanoparticles have an average particle size of 50-70 nm diameter. This Si sample is purchased from Nanostructured & Amorphous Materials Inc. The composition of the electrode laminate is 34% by weight of PFPFOFOMB polymer, and 66% Si nanoparticles. The electrode is cast by a slurry process described below.

Monomer Synthesis

10-Tosyloxy-2,5,8-trioxadecane

Triethlyene glycol monomethylether (10 g, 61 mmol) was dissolved in THF (50 mL) and cooled to 0° C. in an ice bath. A solution of KOH (5.6 g, 100 mmol) in 10 mL water was slowly added to the mixture, and then a solution of TsCl (9.5 g, 50 mmol) in 20 mL THF was added drop-wise over 20 min. with vigorous stirring. After stirring overnight in an ice bath, the mixture was poured into distilled water (200 mL) and extracted with $CH_2Cl_2$ (2×100 mL). The combined organic solutions were washed with saturated $NaHCO_3$ solution (2×100 mL), distilled water (2×100 mL), dried over $MgSO_4$, and concentrated under reduced pressure to give 15.7 g as a clear colorless oil in 99% yield. $^1$H NMR (300 MHz, $CDCl_3$) δ 2.3 (s, 3H), 3.22 (s, 3H), 3.28-3.70 (m, 10H), 4.04 (t, 2H), 7.24 (d, 2H), 7.68 (d, 2H).

ethyl acetate (50/50) as eluant. TLC (ethyl acetate/Hexane=1/1) $R_f$=0.12. The fraction at Rf=0.12 was collected and concentrated to give 5.7 product in 60% yield. $^1$H NMR (300 MHz, $CDCl_3$) δ 2.34 (t, 4H), 2.77 (t, 4H), 3.10-3.60 (m, 22H), 7.40-7.60 (m, 6H).

Polymerization

Poly(2,7-9,9-dioctylfluorene-co-2,7-9,9-(di(oxy-2,5,8-trioxadecane))fluorine-co-2,7-fluorenone-co-2,5-1-methylbenzoic ester): A mixture of 9,9-dioctylfluorene-2,7-diboronic acid bis(1,3-propanediol) ester (1.10 g, 1.97 mmol), 9,9-(di(oxy-2,5,8-trioxadecane))fluorine (0.44 g, 0.71 mmol) 2,7-dibromo-9-fluorenone (0.24 g, 0.72 mmol), methyl2,5-dibromobenzoate (0.21 g, 0.72 mmol), $(PPh_3)_4Pd$ (0) (0.082 g, 0.072 mmol) and several drops of Aliquat 336 in a mixture of 13 mL of THF and 5 mL of 2 M $Na_2CO_3$ solution was refluxed with vigorous stirring for 72 h under an argon atmosphere. After reaction stopped, the solution was concentrated by vacuum evaporation and the polymer was precipitated from methanol. The resulting polymer was further purified by precipitating from methanol twice.

PFPFOFOMB and Electrode Characterization

Circular voltamegram (CV) of PFPFOMB was measured against a Li reference. The Polymer was coated on Cu current collector. Electrolyte is 1M $LiPF_6$ in EC/EMC/DMC 1/1/1 with 10% FEC electrolyte. The conditions for CV are polymer weight 70 microgram, voltage step 0.2 mV/s, area 1.6 cm2.

Figure 8:
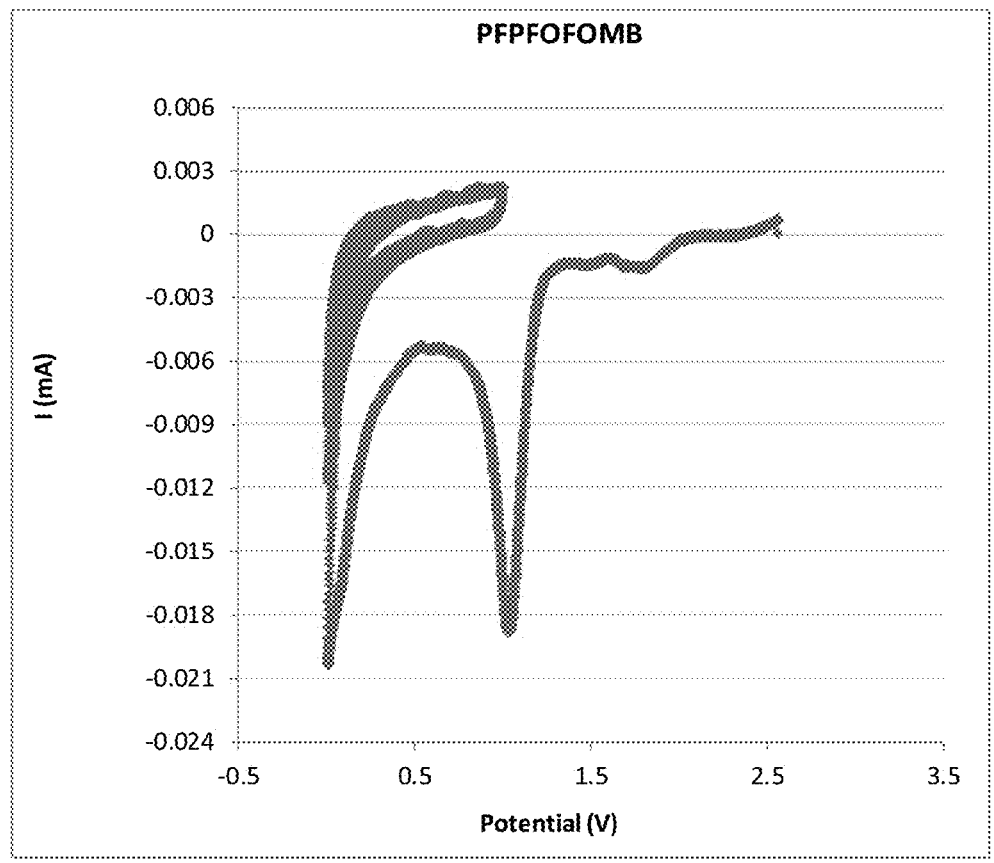
FIG. 8 is the CV of the PFPFOFOMB polymer vs. Li/Li+.

FIG. 8 is the CV of the PFPFOFOMB polymer vs. Li/Li+. The swelling rate of this PFPFOFOMB polymer was also measured against the 1M LiPF6, EC/DEC (1:1, wt) electrolyte, and compared with the PFFOMB polymers. The film thickness is controlled around 10 micron. PFPFOFOMB polymer has much higher swelling in the electrolyte compared to the PFFOMB polymer.

Figure 9:
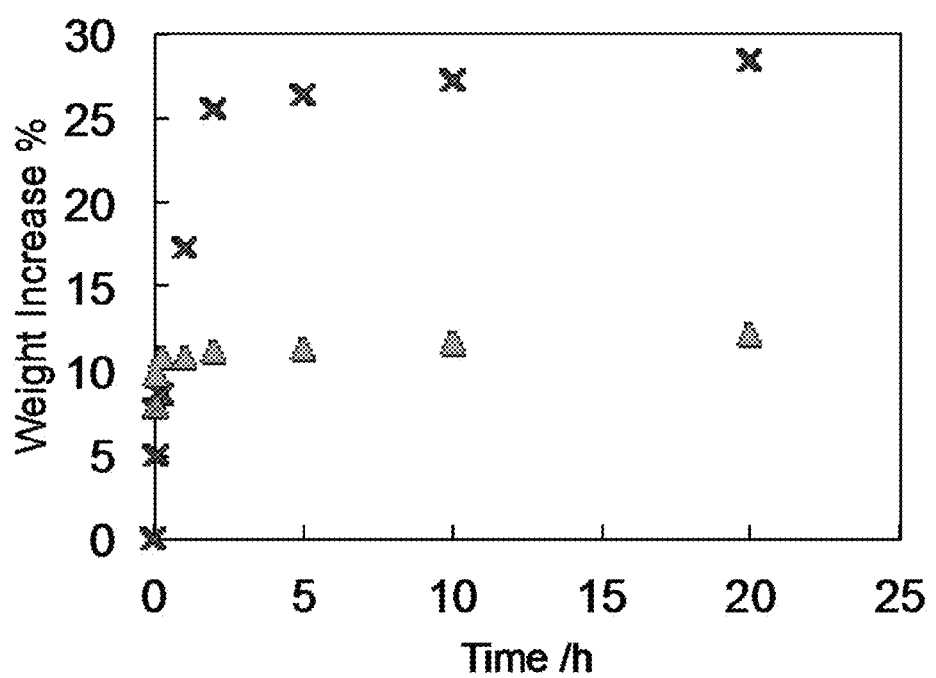
FIG. 9 is a test of PFPFOFOMB (cross) vs. PFFOMB (triangle) polymers.

FIG. 9 is a test of PFPFOFOMB (cross) vs. PFFOMB (triangle) polymers. The polymer binder solution was made by dissolving 90 mg of polymer binder in 2.6 mL of N-methylpyrrolidone (NMP) solution with magnetic stirring. 180 mg of the Si nano powder was added into the binder solution and sonicated for 2 minutes to make uniformed slurry. The slurry was coated on a piece of Cu current collector with a doctor blade at a gap of 25 µm. All the processes were done in the inert atmosphere glove box. The laminate was vacuum dried at 120° C. over night. The laminate thickness 12 µm. The electrode was pouch out with a ⁹⁄₁₆" pouch. The weight of active materials Si is 0.28 mg. The electrode was assembled into a coin cell with Li metal counter electrode, Celgard® 2500 separator and 1M LiPF$_6$ in EC/EMC/DMC 1/1/1 with 10% FEC electrolyte. FIG. 1 shows the coin cell cycling test in 30° C. temperature oven at C/10 current (0.12 mA) between 0.01V-1V voltage range. The C-rate calculation of the Si based electrode is assuming the Si has the theoretical capacity of 4200 mAh/g.

Figure 10:
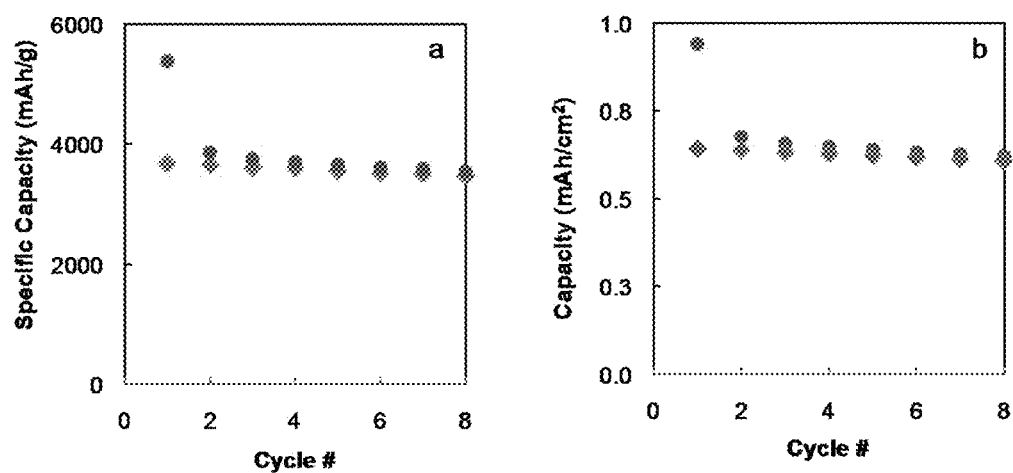
FIG. 10 is the cycling capacity of the Si/PFPFOFOMB electrode at C/10 rate. (a) The electrode specific capacity based on Si weight. (b) The electrode area specific capacity.

FIG. 10 is the cycling capacity of the Si/PFPFOFOMB electrode at C/10 rate. (a) The electrode specific capacity based on Si weight. (b) The electrode area specific capacity. The C-rate performance of the Si/PFPFOFOMB composite electrode was also tested in 1 M LiPF6 EC/DEC (3:7 weight) 30% FEC and reported in FIG. 11.

Figure 11:
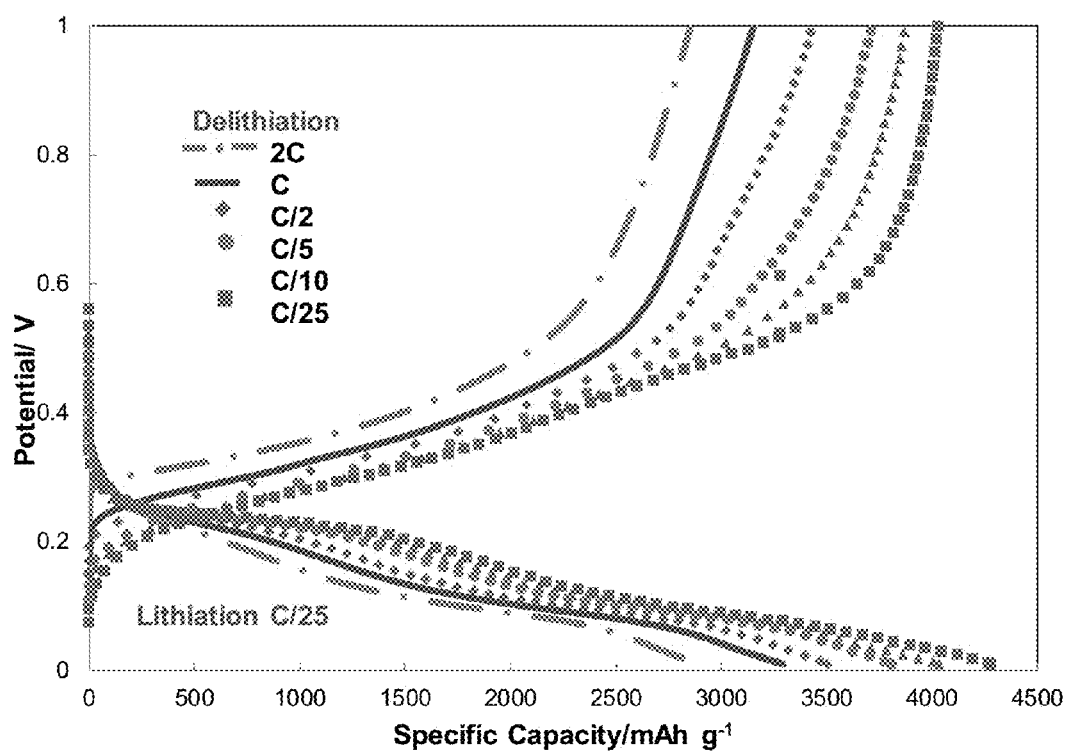
FIG. 11 is the C/25 lithiation and variable delithiation rate of the composite electrode.

FIG. 11 is the C/25 lithiation and variable delithiation rate of the composite electrode. The PFPFOFOMB polymer based Si electrode has much improved performance and can deliver the full theoretical capacity of the Si particle (3500 mAh/g) with good rate retention. The adhesion of PFPFO-FOMB/Si is much stronger than that of the PFFOMB/Si based system. Adhesion and swelling are keys for the improve performance of the PFPFOFOMB conductive polymer over PFFOMB polymer.

This invention has been described herein in considerable detail to provide those skilled in the art with information relevant to apply the novel principles and to construct and use such specialized components as are required. However, it is to be understood that the invention can be carried out by different equipment, materials and devices, and that various modifications, both as to the equipment and operating procedures, can be accomplished without departing from the scope of the invention itself.

What we claim is:

1. A polymeric composition with repeating units of the formula:

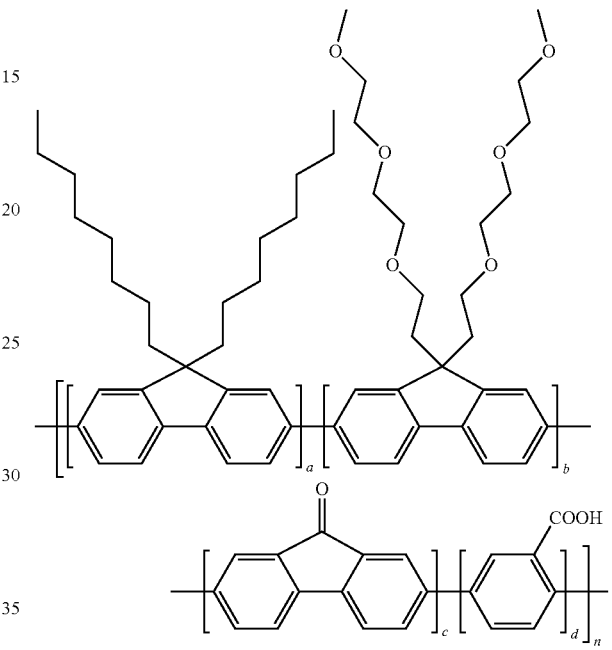

wherein a=1-1,000, b=1-1,000, c=1-1,000, d=1-1,000 where n=1-100,000.

2. The polymeric composition of claim 1 wherein: a=b+c+d.

* * * * *